United States Patent
Van Cleve et al.

(10) Patent No.: US 10,036,694 B2
(45) Date of Patent: Jul. 31, 2018

(54) VIBRATING DENSITOMETER INCLUDING AN IMPROVED VIBRATING MEMBER

(75) Inventors: Craig Brainerd Van Cleve, Lyons, CO (US); George Macdonald, Wokingham (GB)

(73) Assignee: Micro Motion, Inc., Boulder, CO (US)

( * ) Notice: Subject to any disclaimer, the term of this patent is extended or adjusted under 35 U.S.C. 154(b) by 233 days.

(21) Appl. No.: 13/814,892

(22) PCT Filed: Nov. 5, 2010

(86) PCT No.: PCT/US2010/055587
§ 371 (c)(1),
(2), (4) Date: Feb. 7, 2013

(87) PCT Pub. No.: WO2012/030353
PCT Pub. Date: Mar. 8, 2012

(65) Prior Publication Data
US 2013/0133418 A1   May 30, 2013

Related U.S. Application Data

(60) Provisional application No. 61/379,051, filed on Sep. 1, 2010.

(51) Int. Cl.
*G01N 9/00* (2006.01)
(52) U.S. Cl.
CPC ....... *G01N 9/002* (2013.01); *G01N 2009/006* (2013.01); *Y10T 29/49* (2015.01); *Y10T 29/49764* (2015.01); *Y10T 29/49826* (2015.01)
(58) Field of Classification Search
CPC ......... G01N 9/00; G01N 9/004; G01N 9/3234
USPC ......................................................... 73/32 A
See application file for complete search history.

(56) References Cited

U.S. PATENT DOCUMENTS

| | | | | |
|---|---|---|---|---|
| 3,044,012 A | * | 7/1962 | Zito et al. | 324/461 |
| 3,093,792 A | * | 6/1963 | Steenfeld et al. | 324/461 |
| 3,175,399 A | * | 3/1965 | Medlar | 73/861.21 |
| 3,176,222 A | * | 3/1965 | Atkisson | 324/666 |

(Continued)

FOREIGN PATENT DOCUMENTS

| | | |
|---|---|---|
| GB | 1510505 | 5/1978 |
| JP | 2003185554 A | 7/2003 |

(Continued)

OTHER PUBLICATIONS

Paliwal, D. N., Ralesh Kumar Pandey, and Triloki Nath. "Free vibrations of circular cylindrical shell on Winkler and Pasternak foundations." *International Journal of Pressure Vessels and Piping* 69.1 (1996): 79-89.*

(Continued)

*Primary Examiner* — Peter Macchiarolo
*Assistant Examiner* — Alexander Mercado
(74) *Attorney, Agent, or Firm* — The Ollila Law Group LLC

(57) ABSTRACT

An apparatus is provided that comprises a vibrating member (402). The vibrating member (402) is for a vibrating densitometer (400). The vibrating member (402) includes one or more apertures (420). The one or more apertures (420) are sized and located in the vibrating member (402) to increase a frequency separation between a resonant frequency of a desired vibrational drive mode and a resonant frequency of one or more undesired vibrational modes.

16 Claims, 6 Drawing Sheets

(56) References Cited

U.S. PATENT DOCUMENTS

| | | | | |
|---|---|---|---|---|
| 3,199,355 A | * | 8/1965 | Simon-Suisse | 73/702 |
| 3,225,588 A | * | 12/1965 | Bournazel et al. | 73/32 R |
| 3,421,077 A | * | 1/1969 | Berwin et al. | 324/663 |
| 3,516,283 A | * | 6/1970 | Abbotts | 73/24.05 |
| 3,618,360 A | * | 11/1971 | Curtis | 73/24.05 |
| 3,623,357 A | * | 11/1971 | Abbotts | 73/32 R |
| 3,626,749 A | * | 12/1971 | Abbotts | 73/32 A |
| 3,805,592 A | | 4/1974 | Miller et al. | |
| 3,863,505 A | * | 2/1975 | Moffatt | 73/702 |
| 3,874,221 A | * | 4/1975 | Lockie | 73/24.05 |
| 4,064,738 A | | 12/1977 | November | |
| 4,129,031 A | * | 12/1978 | Tehon et al. | 73/32 A |
| 4,275,585 A | * | 6/1981 | Buzzell | 73/32 A |
| 4,420,983 A | * | 12/1983 | Langdon | 73/861.18 |
| 6,688,176 B2 | | 2/2004 | Storm et al. | |
| 2006/0027023 A1 | * | 2/2006 | Hobbs | 73/665 |
| 2011/0252884 A1 | * | 10/2011 | Hanscombe et al. | 73/32 A |

FOREIGN PATENT DOCUMENTS

| | | |
|---|---|---|
| RU | 24732 U1 | 8/2002 |
| SU | 360591 A1 | 11/1972 |

OTHER PUBLICATIONS

Axmon, Joakim, Maria Hansson, and Leif Sornmo. "Partial Modal Analysis for Health Assessment of Living Trees." 10th Asia-Pacific Conference on Non-Destructive Testing, n.d. Web. Mar. 13, 2002.*

* cited by examiner

VIBRATING DENSITOMETER INCLUDING AN IMPROVED VIBRATING MEMBER

TECHNICAL FIELD

The present invention relates to, densitometers, and more particularly, to a vibrating densitometer with an improved vibrating member.

BACKGROUND OF THE INVENTION

Densitometers are generally known in the art and are used to measure a density of a fluid. The fluid may comprise a liquid, a gas, a liquid with suspended particulates and/or entrained gas, or a combination thereof. While there are various types of densitometers that operate according to different principles, one type of densitometer that has received great commercial success is a vibrating densitometer. Vibrating densitometers can comprise a vibrating member, such as a cylinder, a conduit, a pipe, a tube, etc. that is exposed to a fluid under test. One example of a vibrating densitometer comprises a conduit cantilever mounted with an inlet end coupled to an existing pipeline or other structure and the outlet end free to vibrate. Alternatively, both the inlet and outlet may be fixed with the portion of the conduit between the inlet and outlet vibrating. The conduit can be vibrated at resonance and the resonant frequency can be measured. As is generally known in the art, the density of the fluid under test can be determined by measuring the reduced resonant frequency of the conduit. According to well-known principles, the resonant frequency of the conduit will vary inversely with the density of the fluid that contacts the conduit. Therefore, while some vibrating densitometers are capable of measuring a density of a liquid, viscous damping caused by the liquid on the outside of the cylinder can reduce the measurement capabilities of vibrating densitometers. Liquid vibrating densitometers thus use vibrating pipes or tubes that have the fluid only on the inside, while gas vibrating densitometers typically are immersed in the fluid, having gas both on the inside and the outside of the cylinder. Therefore, typically, vibrating densitometers are used to measure a density of a gas.

FIG. 1 shows a prior art immersed densitometer 10. The prior art densitometer 10 may be configured to measure a density of a fluid, such as a liquid or a gas, for example. The densitometer 10 includes a housing 11 with a vibrating member 12 located at least partially within the housing 11. A portion of the housing 11 is cut away to show the vibrating member 12. The densitometer 10 may be placed in-line in an existing pipeline, for example. Alternatively, the housing 11 may comprise closed ends with apertures to receive a fluid sample, for example. Therefore, while flanges are not shown, in many instances, the housing 11 or the vibrating member 12 may include flanges or other members for operatively coupling the densitometer 10 to a pipeline or similar fluid delivering device in a fluid-tight manner. According to the example shown, the vibrating member 12 is cantilever mounted to the housing 11. The vibrating member 12 is shown coupled to the housing 11 at an inlet end 13 with the outlet end 14 free to vibrate.

According to the example shown, the vibrating member 12 also includes a plurality of fluid apertures 15 near the inlet end 13. The fluid apertures 15 can be provided to allow some of the fluid entering the densitometer 10 to flow between the housing 11 and the vibrating member 12. Therefore, the fluid contacts the inside as well as the outside surfaces of the vibrating member 12. This is particularly helpful when the fluid under test comprises a gas because a greater surface area is exposed to the gas. In other examples, apertures may be provided in the housing 11 to expose the fluid under test to the outer surface of the vibrating member 12 and therefore, the apertures 15 are not required in the vibrating member 12.

Further shown in FIG. 1 is a driver 16 and a vibrating sensor 17 positioned within a cylinder 50. The driver 16 and vibrating sensor 17 are shown as comprising coils, which are well known in the art. If an electric current is provided to the coil, a magnetic field is induced in the vibrating member 12 causing the vibrating member 12 to vibrate. Conversely, the vibration of the vibrating member 12 induces a voltage in the vibrating sensor 17. The driver 16 receives a drive signal from a meter electronics 18 in order to vibrate the vibrating member 12 at one of its resonant frequencies in one of a plurality of vibration modes, including for example simple bending, torsional, radial, or coupled type. The vibrating sensor 17 detects the vibration of the vibrating member 12, including the frequency at which the vibrating member 12 is vibrating and sends the vibration information to the meter electronics 18 for processing. As the vibrating member 12 vibrates, the fluid contacting the vibrating member's wall vibrates along with the vibrating member 12. The added mass of the fluid contacting the vibrating member 12 lowers the resonant frequency. The new, lower, resonant frequency of the vibrating member 12 is used to determine the density of the fluid as is generally known in the art according to a previously determined correlation, for example.

As is generally known, to obtain accurate density measurements, the resonant frequency used to measure the density of the fluid must be very stable. This is particularly true when the fluid comprises a gas as the resonant frequency changes by a smaller amount compared to liquid. One prior art approach to achieve the desired stability is to vibrate the vibrating member 12 using a radial vibration mode. In contrast to a bending vibration mode, for example, where the longitudinal axis of the vibrating member translates and/or rotates away from its rest position, in a radial vibration mode, the longitudinal axis of the vibrating member remains essentially stationary while at least a part of the vibrating member's wall translates and/or rotates away from its rest position. Radial vibration modes are preferred in straight conduit densitometers, such as the prior art densitometer 10 shown in FIG. 1 because radial vibration modes are self-balancing and thus, the mounting characteristics of the vibrating member are not as critical compared to some other vibration modes. One example radial vibration mode is a three-lobed radial vibration mode. An example of the change in shape of the vibrating member's wall during a three-lobed radial vibration mode is shown in FIG. 3.

If the vibrating member 12 is perfectly round and has a perfectly uniform wall thickness, there is only one three-lobed radial vibration mode. However, due to design tolerances, this is usually impractical. Consequently, when a manufacturer attempts to make a perfectly round vibrating member 12 with a perfectly uniform wall thickness, small imperfections result in two three-lobed radial vibrations that vibrate at two different resonant frequencies, which are very close to one another. The three-lobed radial vibrational mode with the lower resonant frequency will vibrate with the peaks and valleys as shown in FIG. 3 aligned with the thinner walled portions while the higher frequency will vibrate with the peaks and valleys at the thicker wall portions. The frequency separation between the two modes is typically very small and may be less than a hertz. With two resonant frequencies so close together, a density determination is impractical because an operator will often not be able to distinguish the vibrational frequencies to determine what mode is being driven into vibration and thus, the correct density.

In some prior art densitometers, this problem is addressed by tuning the radial mode so that it has at least a minimum frequency separation between the two three-lobed radial vibrational modes as well as from the other vibration modes, such as the two lobed modes or the four lobed modes. While the tuning can be accomplished according to a variety of techniques, one prior art approach tuning method is by grinding the vibrating member's wall in axially aligned strips so the vibrating member has different thicknesses in different circumferential regions. This is shown in FIG. 1, but in more detail in FIG. 2.

FIG. 2 shows the vibrating member 12 taken along line 2-2 of FIG. 1. FIG. 2 is shown with reference angles shown as well. The reference angles are taken where the driver 16 and the vibrating sensor 17 are positioned at 0°. However, the angles are merely shown as an example and other reference coordinate angles may be used.

As shown, the vibrating member 12 comprises varying wall thicknesses around the circumference of the conduit. For example, the vibrating member 12 may originally comprise a thickness of approximately 0.005 inches (0.125 mm). The driver 16 and the vibrating sensor 17 are centered on one of these thick walled regions. Starting at approximately 15° and spacing uniformly around the circumference of the vibrating member 12 at approximately 30° intervals, six regions of the wall of the vibrating member 12 are ground down to approximately 0.004 inches (0.100 mm). Typically, the thickness of the wall is reduced by using a mandrel that has movable segments moved into position by hydraulic pressure. When the mandrel is pressurized, the movable segments move out the required amount to contact the vibrating member 12 and the thinner regions are ground. By grinding the vibrating member wall thickness in various circumferential regions, the resonant frequencies of the two three-lobed radial vibration modes are separated from one another. With the spacing between the thin regions being approximately 30°, the higher frequency three-lobed radial mode will be offset from the lower frequency three-lobed radial mode by approximately 15°. In one example, the lower frequency three-lobed vibrational mode will vibrate with the peaks and valleys centered on the thin and thick portions while the higher frequency three-lobed vibrational radial mode will have the peaks and vales half-way between the thin and thick regions.

The above-mentioned process has several problems. The hydraulic mandrel is at the limit of its dimensional capability. In other words, the grinding is extremely precise and is often close to or even beyond the design capabilities of the hydraulically operated mandrel. Further, non-destructive measurement of the vibrating member wall thickness is extremely difficult. Consequently, the acceptable product yield is low, resulting in an increased cost associated with the tuning method. In addition, in order to drive the lower frequency three-lobed radial vibrational mode, the driver 16 needs to be positioned opposite the thick walled portion. However, the difference between the thick and thin walled portions is typically extremely small at 0.001 inches (0.025 mm). Therefore, proper placement is very difficult. Further, as shown in FIG. 2, it is extremely difficult to match the grinding of each of the thin walled portions to one another.

Therefore, there exists a need for a method and apparatus for improving vibrating densitometers. Specifically, there exists a need for a vibrating densitometer with increased vibration mode separation while maintaining a higher product yield. The present invention solves this and other problems and an advance in the art is achieved.

SUMMARY OF THE INVENTION

An apparatus including a vibrating member for a vibrating densitometer is provided according to an embodiment of the invention. According to an embodiment of the invention, the vibrating member includes one or more apertures sized and located in the vibrating member to increase a frequency separation between a resonant frequency of a desired vibrational drive mode and a resonant frequency of one or more undesired vibrational modes.

A method for forming a vibrating densitometer is provided according to an embodiment of the invention. According to an embodiment of the invention, the vibrating densitometer includes a vibrating member adapted to vibrate at one or more resonant frequencies. The method comprises a step of forming one or more apertures in the vibrating member to increase a frequency separation between a resonant frequency of a desired vibrational drive mode and a resonant frequency of at least a second undesired vibrational mode.

ASPECTS

According to an aspect of the invention, an apparatus comprises:
a vibrating member for a vibrating densitometer including one or more apertures sized and located in the vibrating member to increase a frequency separation between a resonant frequency of a desired vibrational drive mode and a resonant frequency of one or more undesired vibrational modes.

Preferably, the apparatus further comprises a housing wherein the vibrating member is located at least partially inside the housing.

Preferably, the vibrating member further comprises a first end cantilever mounted to the housing such that a second end opposite the first end is free to vibrate.

Preferably, the one or more apertures extend to the second end of the vibrating member.

Preferably, the one or more apertures are formed proximate to, but not extending through, the second end.

Preferably, the apparatus further comprises a driver and one or more vibrating sensors.

Preferably, the desired vibrational drive mode comprises a first three-lobed radial vibrational mode and an undesired vibrational mode of the one or more undesired vibrational comprises a second three-lobed radial vibrational mode.

According to another aspect of the invention, a method for forming a vibrating densitometer including a vibrating member adapted to vibrate at one or more resonant frequencies comprises a step of:
forming one or more apertures in the vibrating member to increase a frequency separation between a resonant frequency of a desired vibrational drive mode and a resonant frequency of at least a second undesired vibrational mode.

Preferably, the method further comprises steps of:
vibrating the vibrating member in the desired vibrational drive mode and the at least second undesired vibrational mode; and
determining a frequency separation between a resonant frequency of the vibrational drive mode and a resonant frequency of the at least second undesired vibrational mode.

Preferably, the one or more apertures comprise preliminary apertures with a size smaller than a desired size and wherein after the step of forming one or more apertures in the vibrating member, the method further comprises steps of:
vibrating the vibrating member in the desired drive mode;
determining a resonant frequency of the desired drive mode; and
determining the desired aperture size based on a correlation between aperture size and frequency.

Preferably, the method further comprises a step of coupling a first end of the vibrating member to a housing, such that at least a portion of the vibrating member is located within the housing.

Preferably, the step of coupling the first end of the vibrating member to the housing comprises cantilever mounting the first end to the housing such that a second end of the vibrating member opposite the first end is free to vibrate.

Preferably, the one or more apertures are formed proximate to, but not extending through, the second end.

Preferably, the one or more apertures extend through the second end of the vibrating member.

Preferably, the method further comprises steps of positioning a driver and one or more vibrating sensors proximate the vibrating member to induce and sense vibrations in the vibrating member.

Preferably, the desired drive mode comprises a first three-lobed radial vibrational mode and an undesired vibrational mode of the one or more undesired vibrational modes comprises a second three-lobed radial vibrational mode.

DETAILED DESCRIPTION OF THE INVENTION

FIGS. 4-8 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 4:
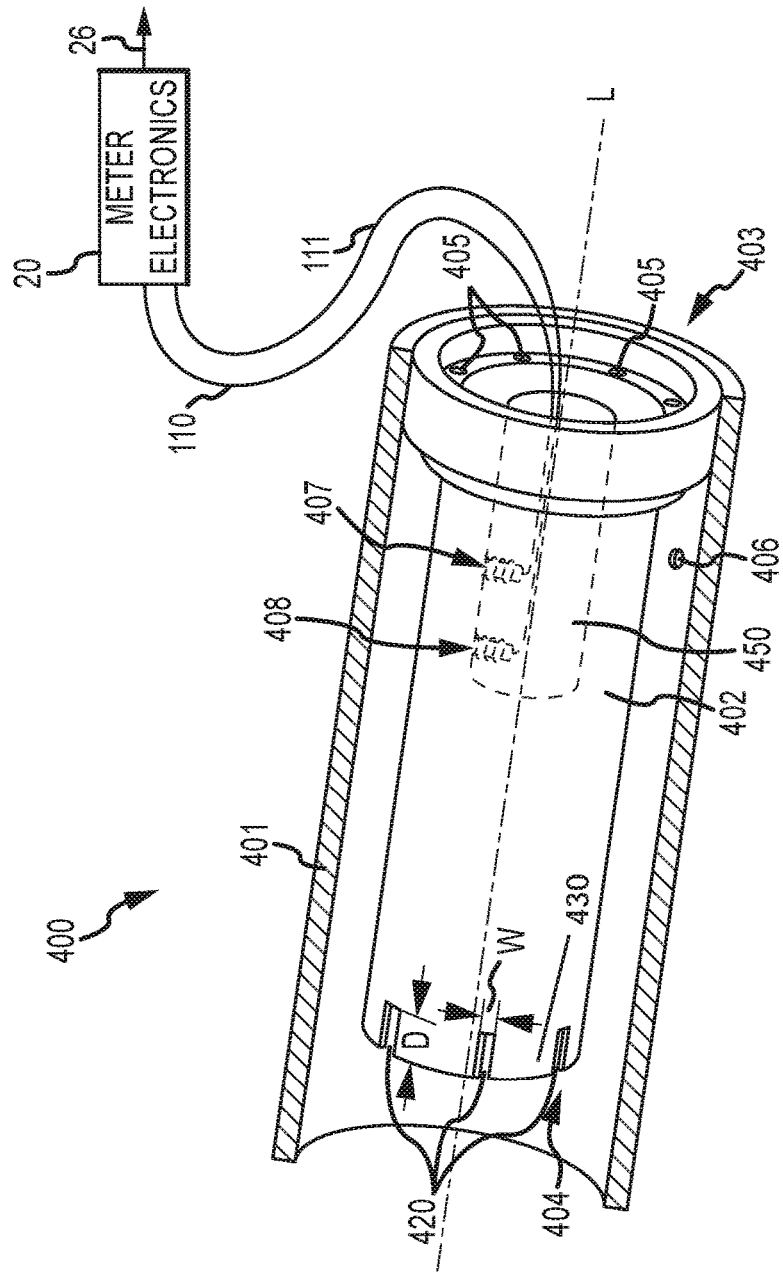
FIG. 4 shows a vibrating densitometer according to an embodiment of the invention.

FIG. 4 shows a vibrating densitometer 400 according to an embodiment of the invention. The vibrating densitometer 400 may be configured to determine a density of a fluid, such as a gas, a liquid, a liquid with entrained gas, a liquid with suspended particulates, or a combination thereof. Due to viscous damping, the vibrating densitometer 400 is typically used to measure a density of a gas rather than a density of a liquid. According to the embodiment shown, the vibrating densitometer 400 comprises a housing 401 and a vibrating member 402 located at least partially within the housing 401. The vibrating member 402 is shown as comprising a cylindrical tube; however, the vibrating member 402 may comprise other configurations, such as a rectangular shaped conduit, for example. The vibrating member 402 is shown cantilever mounted with the vibrating member 402 coupled to the housing 401 at a first end 403 and with a second end 404 free to vibrate within the housing 401. In some embodiments, a portion of the first end 403 of the vibrating member 402 may extend beyond the housing 401. This may allow the vibrating member 402 to be coupled to a pipeline or other fluid delivering system in a fluid-tight manner. Alternatively, in the embodiment shown, the housing 401 could include flanges (not shown) or the like to make the fluid-tight coupling. Furthermore, in some embodiments, the housing 401 proximate the second end 404 may be sealed off to retain a sample fluid under test within the housing 401. According to an embodiment of the invention, the sample fluid under test may enter the vibrating densitometer 400 at the first end 403. For example, the fluid under test may flow into the interior of the vibrating member 402 or flow along the exterior of the vibrating member 402 via fluid apertures 405. Alternatively, the sample fluid under test may enter the vibrating densitometer 400 through one or more optional fluid apertures 406 formed in the housing 401. While one fluid aperture 406 is shown, the housing 401 may include more than one fluid aperture 406 or may not include any fluid apertures 406. The fluid apertures may allow both the first and second ends of the housing 401 to be sealed off in a fluid-tight manner. In another alternative embodiment, the fluid may enter the vibrating densitometer 400 at the second end 404.

According to an embodiment of the invention, the vibrating densitometer 400 can include one or more drivers 407. The driver 407 can be adapted to vibrate the vibrating member 402 in one or more vibrational modes. While the driver 407 is shown positioned closer to the first end 403, it should be appreciated that the driver 407 may be located at any desired point along the vibrating member 402. Furthermore, while the driver 407 is shown located within a central tower 450 positioned within the vibrating member 402, in some embodiments, the driver 407 is positioned between the housing 401 and the vibrating member 402, for example. In the embodiment shown, the driver 407 comprises a coil. The coil can receive an electrical signal from a meter electronics 20 in the form of a drive signal over path 110 to vibrate the vibrating member 402 in a desired vibrational drive mode.

According to an embodiment of the invention, the vibrating densitometer 400 can also include a vibrating sensor 408. While the vibrating sensor 408 is shown coaxially aligned with the driver 407, in other embodiments, the vibrating sensor 408 may be coupled to the vibrating member 402 in other locations. The vibrating sensor 408 can transmit a signal to the meter electronics 20 via path 111. The meter electronics 20 can process the signals received by the vibrating sensor 408 to determine a resonant frequency of the vibrating member 402. If a fluid under test is present, the resonant frequency of the vibrating member 402 will change inversely proportional to the fluid density as is known in the art. The proportional change may be determined during an initial calibration, for example. In the embodiment shown, the vibrating sensor 408 also comprises a coil. The vibrating sensor 408 is similar to the driver 407;

however, while the driver 407 receives a current to induce a vibration in the vibrating member 402, the vibrating sensor 408 uses the motion of the vibrating member 402 created by the driver 407 to induce a voltage. Coil drivers and sensors are well known in the art and a further discussion of their operation is omitted for brevity of the description. Furthermore, it should be appreciated that the driver 407 and vibrating sensor 408 are not limited to coils, but rather may comprise a variety of other well-known vibrating components, such as piezo-electric sensors, for example. Therefore, the present invention should in no way be limited to coils. Furthermore, those skilled in the art will readily recognize that the particular placement of the driver 407 and sensor 408 can be altered while remaining within the scope of the present invention.

Figure 1:
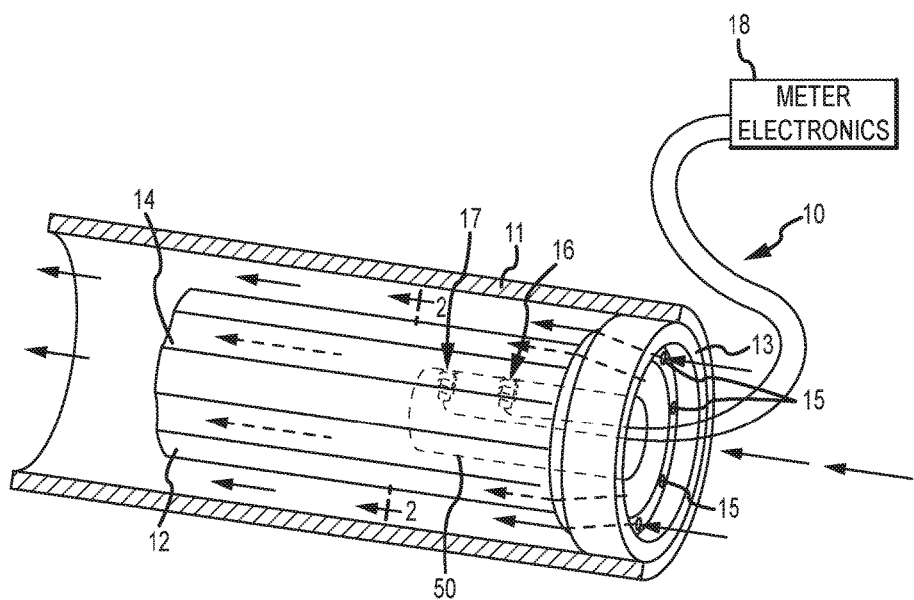
FIG. 1 shows a prior art vibrating densitometer.
Figure 2:
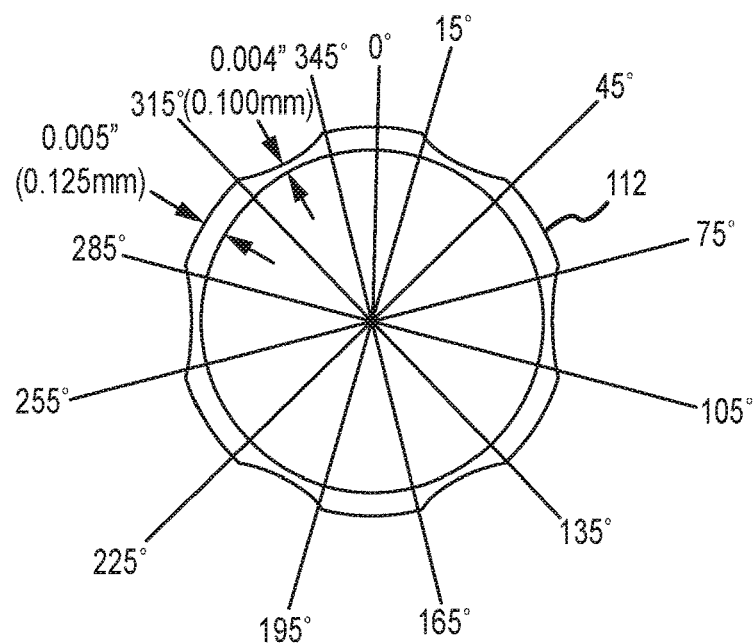
FIG. 2 shows a prior art vibrating member.
Figure 3:
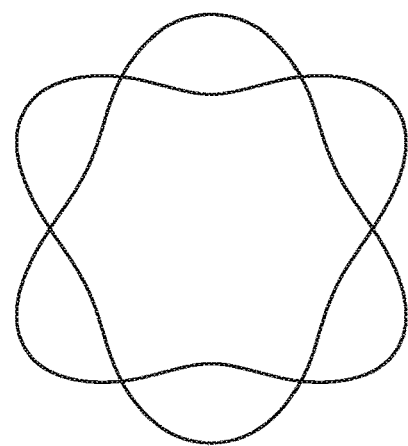
FIG. 3 shows a three-lobed radial vibration.

According to an embodiment of the invention, the vibrating member 402 comprises six apertures 420. Each adjacent pair of apertures 420 includes a mass 430 in between. In one embodiment, the apertures 420 are spaced every 60° on center around the circumference of the vibrating member 402. According to an embodiment of the invention, the six apertures 420 are substantially evenly spaced around a circumference of the vibrating member 402. For example, with reference to the angles depicted in FIG. 2, the apertures 420 can be formed starting at 15° and spaced every 60°, where the driver 407 and/or vibrating sensor 408 are positioned proximate the vibrating member 402 opposite 0°. According to an embodiment of the invention, the apertures 420 are sized and located in order to increase a frequency separation between the desired drive mode vibrational frequency and at least a second vibrational frequency. As discussed above, as one example, the apertures 420 are sized and located in order to increase a frequency separation between the lower frequency three-lobed radial mode and the higher frequency three-lobed radial mode. Advantageously, the vibrating member 402 can be made substantially uniform in wall thickness (or as close as manufacturing tolerances will allow) and the apertures 420 can replace the axial strips of reduced thickness as seen in the prior art cylinder 12.

Returning to FIG. 4, according to an embodiment of the invention, the apertures 420 are formed to separate a resonant frequency of a desired vibrational drive mode of the vibrating member 402 from one or more undesired vibrational frequencies. For example, as mentioned above with regard to the prior art vibrating densitometer 10, one desired vibrational mode is a three-lobed radial vibrational mode. More particularly, the resonant frequency of the desired vibrational mode is the lower frequency three-lobed radial vibrational mode. Therefore, according to an embodiment of the invention, the apertures 420 are provided to separate the two three-lobed radial vibrational mode resonant frequencies. However, it should be appreciated that in other embodiments, the desired vibrational mode may not comprise the lower frequency three-lobed radial vibrational mode, and therefore, the present invention should not be limited to this particular vibrational mode. However, the three-lobed radial vibrational frequencies are used in the present application as one particular example. Those skilled in the art will readily recognize how to modify the present application in order separate the resonant frequencies of other desired vibrational modes. Further, the apertures 420 may also separate the desired drive mode frequency from other vibrational modes, such as the bending mode, and not just the higher frequency three-lobed radial vibrational mode.

According to an embodiment of the invention, the vibrating member 402 comprises six apertures 420. In one embodiment, the apertures 420 are spaced every 60° on center around the circumference of the vibrating member 402. According to an embodiment of the invention, the six apertures 420 are substantially evenly spaced around a circumference of the vibrating member 402. For example, with reference to the angles depicted in FIG. 2, the apertures 420 can be formed starting at 15° and spaced every 60°, where the driver 407 and/or vibrating sensor 408 are positioned proximate the vibrating member 402 opposite 0°. According to an embodiment of the invention, the apertures 420 are sized and located in order to increase a frequency separation between the desired drive mode vibrational frequency and at least a second vibrational frequency. As discussed above, as one example, the apertures 420 are sized and located in order to increase a frequency separation between the lower frequency three-lobed radial mode and the higher frequency three-lobed radial mode. Advantageously, the vibrating member 402 can be made substantially uniform in wall thickness (or as close as manufacturing tolerances will allow) and the apertures 420 can replace the axial strips of reduced thickness as seen in the prior art cylinder 12.

According to an embodiment of the invention, the apertures 420 are substantially rectangular. Therefore, in the embodiment shown, the apertures 420 comprise a depth, D and a width, W. The apertures 420 also comprise a height, but the height is simply dependent upon the thickness of the vibrating member's wall. According to an embodiment of the invention, the depth, D of the apertures extends substantially parallel to a longitudinal axis, L of the vibrating member 402. According to an embodiment of the invention, the width, W of the apertures 420 extend substantially along the circumference of the vibrating member 402. While other orientations may be used, the orientation used in the present application will aid in an understanding of how to form the one or more apertures 420 to achieve a desired frequency separation according to an embodiment of the invention.

As explained below, there is often a trade-off made between frequency separation and meter sensitivity when forming the aperture depth and aperture width. As the depth increases, the resonant frequency of the vibrating member 402 decreases and the separation between the two three-lobed radial vibrational frequencies increases. However, as the depth increases, the surface area of the vibrating member 402 decreases. This decrease in the surface area results in a decrease in the sensitivity of the vibrating densitometer because less of the fluid under test can contact the surface of the vibrating member 402. Similarly, as the width increases, the frequencies initially decrease and once the width reaches a threshold width, the frequencies increase. This is explained in detail below with the description that accompanies FIG. 6.

Figure 5:
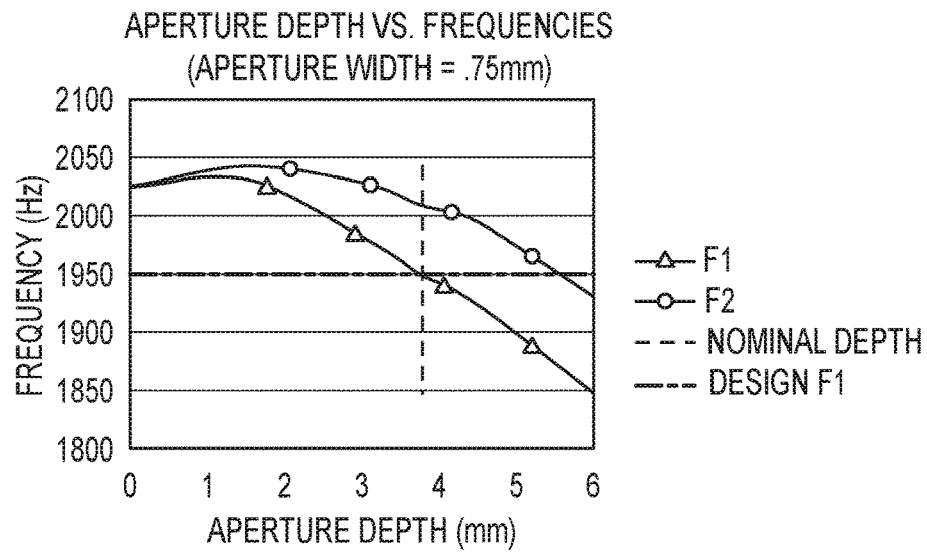
FIG. 5 shows a graph of aperture depth versus frequency.

FIG. 5 shows a graph of aperture depth versus frequency according to an embodiment of the invention. The graph shown in FIG. 5 was generated using an aperture width of approximately 0.03 inches (0.75 mm). In both FIGS. 5 & 6, f1 is the lower three-lobed radial vibrational frequency (desired drive mode in this example) and f2 is the upper three-lobed radial vibrational frequency. However, similar graphs could be generated using other aperture widths. Furthermore, it should be appreciated that the particular values provided on the graph will depend upon a variety of variables including, but not limited to, the material, the thickness, the length, the circumferential radius of the cylinder 402, etc. Therefore, the particular values depicted should in no way limit the scope of the present invention.

As can be seen in FIG. 5, as the aperture depth increases, the separation between the lower three-lobed radial vibrational frequency and the upper three-lobed radial vibrational frequency increases. Therefore, the depth can be set such that the desired frequency separation is achieved. Alternatively, the depth can be set so that the lower three-lobed radial vibrational frequency is at a desired nominal vibrational drive frequency, for example. In this case, the nominal drive frequency was set to approximately 1950 Hz. This desired drive frequency resulted in an aperture depth of approximately 0.14 inches (3.6 mm). With this aperture depth, the two modes are separated by approximately 65 Hz.

Figure 6:
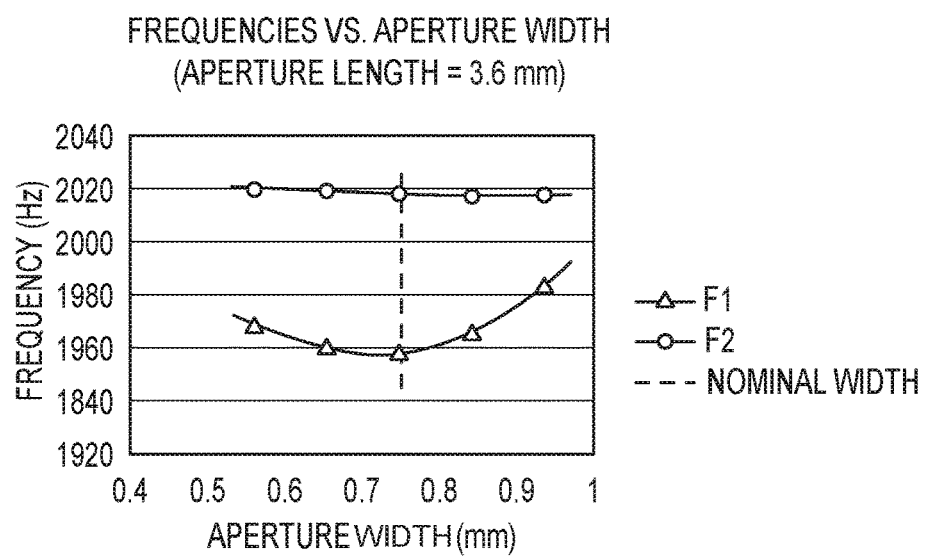
FIG. 6 shows a graph of aperture width versus frequency.

FIG. 6 shows a graph of aperture width versus frequency according to an embodiment of the invention. As can be appreciated, the graph of FIG. 6 can be used in a similar manner to the graph of FIG. 5 to determine a desired aperture width. The graph of FIG. 6 Was generated using an aperture depth of approximately 0.14 inches (3.6 mm); however, similar graphs could be generated using different aperture depths. As can be seen, the frequency separation between the two three-lobed radial vibrational modes increases until approximately 0.03 inches (0.75 mm) at which point, the frequency separation decreases as the lower frequency radial mode increases. This increase in frequency separation is due to the fact that initially, widening the apertures 420 decreases the stiffness at the locations of maximum bending of the lower frequency three-lobed radial mode. However, the locations of the apertures 420 are also near the points of maximum vibrational amplitude. Therefore, eventually, widening of the apertures 420 has the effect of decreasing the vibrating mass, thereby increasing the vibrational frequency. According to an embodiment of the invention, the aperture width can be chosen to maximize the separation between the upper and lower three-lobed radial vibrational frequencies.

As mentioned above, the charts shown in FIGS. 5 & 6 are merely examples of possible correlations that can be generated between the depth and width of the apertures 420 and frequency. Other correlations may be stored in the form of look-up tables or equations, for example. Therefore, if a desired drive frequency is known, a correlating depth and width of the apertures 420 can be determined based on previously obtained correlations. This can be advantageous for a number of reasons. One reason is that acceptable manufacturing yield increases dramatically compared to the prior art approach. In the prior art approach, the vibrating member 12 could not be tested until the wall thickness was already reduced. In contrast, according to an embodiment of the invention, preliminary apertures may be formed in the vibrating member 402. According to an embodiment of the invention, the preliminary apertures may be smaller than the expected final size of the apertures 420. Therefore, with the preliminary apertures formed in the vibrating member 402, the vibrating member 402 can be driven to a resonant frequency in a desired vibrational drive mode and an undesired vibrational mode while the vibrating member 402 is within an aperture-cutting tool (not shown). With the resonant frequency and the frequency separation from the one or more undesired modes determined, the final aperture depth and width can be determined by extrapolating the previously determined correlation to a desired frequency or frequency separation. Therefore, the final desired aperture size can be more accurately determined.

Figure 8:
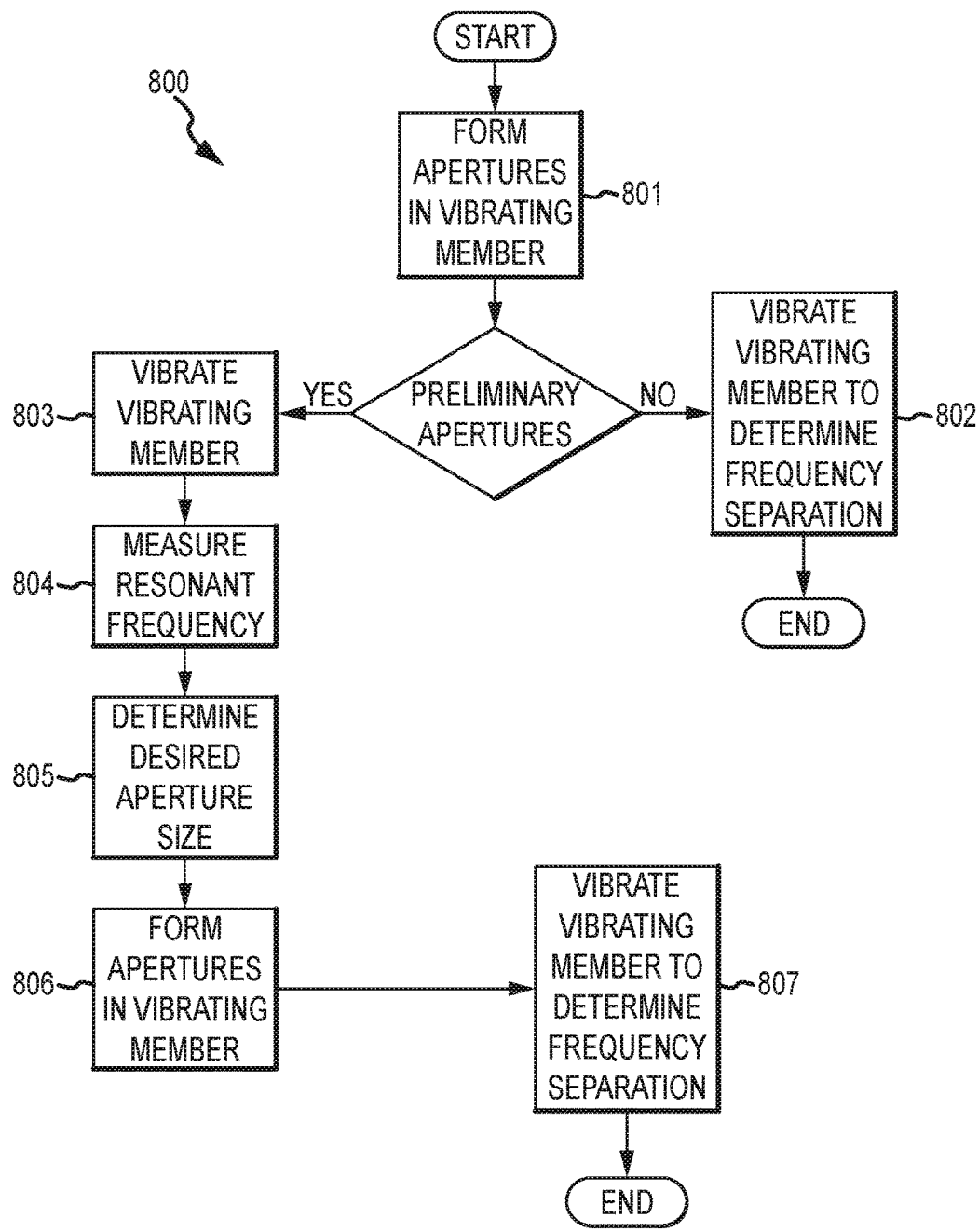
FIG. 8 shows a process for forming a vibrating member for a vibrating densitometer according to an embodiment of the invention.

FIG. 8 shows a process 800 for forming the vibrating member 402 according to an embodiment of the invention. Process 800 starts in step 801 where one or more apertures 420 are formed in the vibrating member 402. The apertures 420 may be formed using a laser cutting procedure, for example. According to an embodiment of the invention, the apertures 420 are formed proximate the second end 404 of the vibrating member 402. The apertures 420 may extend all the way to the second end 404, but do not necessarily have to extend all the way to the second end. With the one or more apertures formed, the process 800 determines if the apertures 420 comprise preliminary apertures or final apertures. Preliminary apertures are apertures formed smaller than the intended final size. If the apertures 420 do not comprise preliminary apertures, and thus comprise the final aperture size, the process 800 proceeds to step 802 where the frequency separation between the desired drive mode and at least a second vibrational mode is determined.

According to an embodiment of the invention, to determine the frequency separation, the vibrating member 402 is vibrated in a desired drive mode. The resonant frequency of the desired drive mode can be measured. The driver 407 and the vibrating sensor 408 can then be repositioned half-way between an aperture 420 and the center of a portion of the second end 404. In one embodiment, the repositioning would be approximately 15°. With the driver 407 and vibrating sensor 408 repositioned, the vibrating member 402 can be vibrated in at least a second vibrational mode. For example, with the driver 407 and vibrating sensor 408 rotated approximately 15°, the meter electronics 20 can vibrate the vibrating member 402 in the higher frequency three-lobed radial vibrational mode. The resonant frequency of the undesired vibrational mode can be determined to determine if the frequency separation has reached a threshold level, which may be predetermined based on a desired frequency separation.

According to an embodiment of the invention, if the apertures formed in step 801 comprise preliminary apertures (apertures that are not the full size of the intended apertures), the process proceeds to step 803 where the vibrating member 402 is vibrated in a desired mode. With the vibrating member 402 vibrating in the desired mode, the resonant frequency of the vibrated mode is determined in step 804.

In step 805, a desired aperture size is determined based on the preliminary apertures, the resonant frequency of the vibrated mode, and a previously determined correlation between aperture size and frequency. The previously determined correlation may be in the form of a chart, such as shown in FIGS. 5 & 6, a look-up table, an equation, etc. For example, if the preliminary apertures were sized at approximately 0.03 inches (0.75 mm) wide with a depth of approximately 0.12 inches (3 mm), according to the correlation shown in FIG. 5, if the desired drive frequency is 1950 Hz, the depth of the apertures should be increased an additional 0.02 inches (0.6 mm). Even if the measured frequency of the vibrating member 402 with the preliminary apertures does not correspond exactly to the correlation, the correlation can be extrapolated based on the measured frequency. For example, if the measured frequency is close to the expected frequency based on the previously generated correlation, the slope of the line in FIG. 5, for example, could be used to determine the desired aperture depth for a desired drive frequency.

In step 806, the apertures 420 are formed to the desired depth and width as determined in step 805.

In step 807, the frequency separation is determined in a manner similar to the steps outlined in step 802 above.

The present invention provides a vibrating member 402 for a vibrating densitometer 400 that has an increase in frequency separation between the desired drive mode frequency and one or more undesired vibrational mode frequencies. In contrast to prior art approaches to separate the vibrational frequencies of the vibrating member 402, which resulted in difficult to manufacture parts and a low acceptable production yield, the present invention forms one or more apertures 420 near a free end of the vibrating member 402. The one or more apertures 420 provide a clear indication of where to position the driver 407 and vibrating sensor 408 in order to vibrate the vibrating member 402 in the desired vibrational mode. Furthermore, the apertures 420 allow the vibrational characteristics of the vibrating member 402 to be tested prior to completion of the apertures 420. This can increase the acceptable yield of production.

The detailed descriptions of the above embodiments are not exhaustive descriptions of all embodiments contemplated by the inventors to be within the scope of the invention. Indeed, persons skilled in the art will recognize that certain elements of the above-described embodiments may variously be combined or eliminated to create further embodiments, and such further embodiments fall within the scope and teachings of the invention. It will also be apparent to those of ordinary skill in the art that the above-described embodiments may be combined in whole or in part to create additional embodiments within the scope and teachings of the invention.

Thus, although specific embodiments of, and examples for, the invention are described herein for illustrative purposes, various equivalent modifications are possible within the scope of the invention, as those skilled in the relevant art will recognize. The teachings provided herein can be applied to other vibrating densitometers, and not just to the embodiments described above and shown in the accompanying figures. Accordingly, the scope of the invention should be determined from the following claims.

We claim:

1. A vibrating densitometer (400), comprising:
a vibrating member (402) including two or more apertures (420) sized with a width (W) and a depth (D), positioned substantially centrally along a longitudinal direction of the vibrating member, and positioned substantially equidistant about the perimeter of the vibrating member (402) to increase a frequency separation between a resonant frequency of a first vibrational drive mode and a resonant frequency of one other vibrational mode, wherein the width (W) is configured to decrease a stiffness and provide a mass (430) at locations of maximum bending of the first vibrational mode to substantially minimize the resonant frequency of the first vibrational drive mode.

2. The vibrating densitometer (400) of claim 1, further comprising a housing (401) wherein the vibrating member (402) is located at least partially inside the housing (401).

3. The vibrating densitometer (400) of claim 2, wherein the vibrating member (402) further comprises a first end (403) cantilever mounted to the housing (401) such that a second end (404) opposite the first end (403) is free to vibrate.

4. The vibrating densitometer (400) of claim 1, further comprising a driver (407) and one or more vibrating sensors (408).

5. The vibrating densitometer (400) of claim 1, wherein the first vibrational drive mode comprises a first three-lobed radial vibrational mode and the one other vibrational mode comprises a second three-lobed radial vibrational mode.

6. The vibrating densitometer (400) of claim 1, wherein the vibrating member further increases the frequency separation between the resonant frequency of the first vibrational drive mode and the resonant frequency of the second vibrational mode by increasing the resonant frequency of the one other vibrational mode.

7. The vibrating densitometer (400) of claim 1, wherein the one or more apertures are substantially rectangular.

8. A method for forming a vibrating densitometer including a vibrating member adapted to vibrate at one or more resonant frequencies, comprising a step of:
forming two or more apertures having a width (W) and a depth (D), positioned substantially centrally along a longitudinal direction of the vibrating member, and positioned substantially equidistant about the perimeter of the vibrating member to increase a frequency separation between a resonant frequency of a first vibrational drive mode and a resonant frequency of a second vibrational mode, wherein the width (W) is selected to decrease a stiffness and provide a mass (430) at locations of maximum bending of the first vibrational mode to substantially minimize the resonant frequency of the first vibrational drive mode.

9. The method of claim 8, further comprising steps of:
vibrating the vibrating member in the first vibrational drive mode and the at least second vibrational mode; and
determining a frequency separation between a resonant frequency of the vibrational drive mode and a resonant frequency of the second vibrational mode.

10. The method of claim 8, wherein the one or more apertures comprise preliminary apertures with a size smaller than a selected size and wherein after the step of forming one or more apertures in the vibrating member, the method further comprises steps of:
vibrating the vibrating member in the first vibrational drive mode;
determining the resonant frequency of the first vibrational drive mode; and
determining the selected aperture size based on a correlation between aperture size and resonant frequency, the correlation between aperture size and frequency derived from one of a chart, a look-up table, and an equation.

11. The method of claim 8, further comprising a step of coupling a first end of the vibrating member to a housing, such that at least a portion of the vibrating member is located within the housing.

12. The method of claim 11, wherein the step of coupling the first end of the vibrating member to the housing comprises cantilever mounting the first end to the housing.

13. The method of claim 8, further comprising steps of positioning a driver and one or more vibrating sensors proximate the vibrating member to induce and sense vibrations in the vibrating member.

14. The method of claim 8, wherein the first vibrational drive mode comprises a first three-lobed radial vibrational mode and the second vibrational mode comprises a second three-lobed radial vibrational mode.

15. The method of claim 8, wherein the vibrating member further increases the frequency separation between the resonant frequency of the first vibrational drive mode and the resonant frequency of the second vibrational mode by increasing the resonant frequency of the one other vibrational mode.

16. The method of claim 8, wherein the one or more apertures are substantially rectangular.

* * * * *

UNITED STATES PATENT AND TRADEMARK OFFICE
CERTIFICATE OF CORRECTION

PATENT NO. : 10,036,694 B2
APPLICATION NO. : 13/814892
DATED : July 31, 2018
INVENTOR(S) : Craig Brainerd Van Cleve and George Macdonald Page 1 of 1

It is certified that error appears in the above-identified patent and that said Letters Patent is hereby corrected as shown below:

In the Specification

Figure 7:
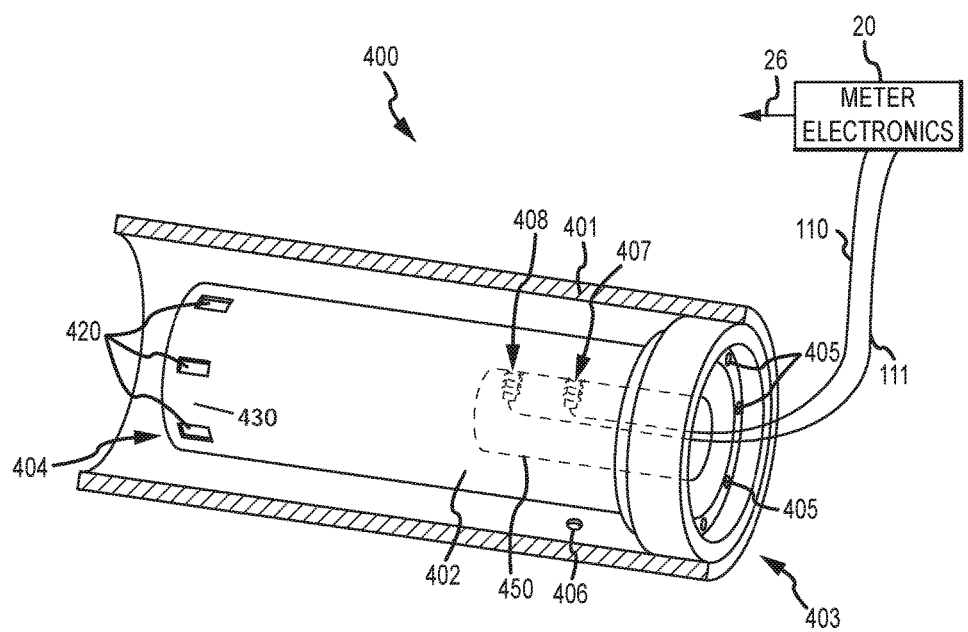
FIG. 7 shows a vibrating densitometer according to another embodiment of the invention.

Column 7, Line 16, cancel the text beginning with "According to an embodiment of the invention," to and ending "cylinder 12." in Column 7, Line 40, and insert the following text:
--According to an embodiment of the invention, the vibrating member 402 further comprises one or more apertures 420. According to an embodiment of the invention, the apertures 420 extend substantially completely through the wall of the vibrating member 402. This is in contrast to the areas of reduced thickness present in the prior art vibrating member 12. According to an embodiment of the invention, the apertures 420 can be formed using a laser cutting procedure; however, those skilled in the art will readily recognize other methods that can be used to form the apertures 420 and the particular method used should in no way limit the scope of the present invention. In the embodiment shown, the apertures 420 are formed in the second end 404 of the vibrating member 402. However, it should be appreciated, that in other embodiments, the apertures 420 may be formed proximate the second end 404, but may not extend all the way to the second end 404 (See FIG. 7, for example). The apertures 420 shown in FIG. 7 are formed proximate the second end 404 but do not extend all the way to the second end 404 and thus, the second end 404 is substantially continuous around the circumference of the vibrating member 402.--

Column 7, Line 67, after the text "comprises six apertures 420." insert the following text:
--Each adjacent pair of apertures 420 includes a mass 430 in between.--

Signed and Sealed this
Sixth Day of November, 2018

Andrei Iancu
*Director of the United States Patent and Trademark Office*